United States Patent [19]

Knapp

[11] Patent Number: 5,688,283
[45] Date of Patent: Nov. 18, 1997

[54] DRILL GUIDE FOR MANDIBULAR STAPLE TRANSOSSEOUS IMPLANTS

[76] Inventor: John G. Knapp, 19928 Farmington Rd., Livonia, Mich. 48152

[21] Appl. No.: 560,541

[22] Filed: Nov. 17, 1995

[51] Int. Cl.⁶ .................................................. A61B 17/56
[52] U.S. Cl. .................. 606/96; 606/80; 606/102; 433/75
[58] Field of Search .......................... 606/96, 98, 80, 606/82, 87, 102, 56, 59; 433/75, 74

[56] References Cited

U.S. PATENT DOCUMENTS

| | | | |
|---|---|---|---|
| 2,181,746 | 11/1939 | Siebrandt | 606/96 |
| 2,644,231 | 7/1953 | Brennan . | |
| 3,414,975 | 12/1968 | Small . | |
| 3,664,022 | 5/1972 | Small . | |
| 3,748,739 | 7/1973 | Thibert . | |
| 3,835,849 | 9/1974 | McGuire | 606/96 |
| 4,214,366 | 7/1980 | Laban . | |
| 4,325,373 | 4/1982 | Slivenko et al. . | |
| 4,360,012 | 11/1982 | McHarrie et al. | 606/59 |
| 4,364,381 | 12/1982 | Sher et al. | 606/96 |
| 4,373,518 | 2/1983 | Kaiser et al. . | |
| 4,439,152 | 3/1984 | Small . | |
| 4,516,937 | 5/1985 | Bosker . | |
| 4,608,972 | 9/1986 | Small . | |
| 4,640,271 | 2/1987 | Lower . | |
| 4,648,841 | 3/1987 | Smith . | |
| 4,713,077 | 12/1987 | Small . | |
| 4,722,687 | 2/1988 | Scortecci . | |
| 4,832,601 | 5/1989 | Linden . | |
| 4,906,189 | 3/1990 | Knapp . | |
| 4,907,577 | 3/1990 | Wu | 606/87 |
| 4,917,604 | 4/1990 | Small . | |
| 5,246,444 | 9/1993 | Schreiber | 606/87 |
| 5,306,278 | 4/1994 | Dahl et al. | 606/96 |
| 5,540,686 | 7/1996 | Zippel et al. | 606/59 |

FOREIGN PATENT DOCUMENTS

| | | |
|---|---|---|
| 2302715 | 10/1976 | France . |
| 3736977 | 7/1988 | Germany . |
| 770696 | 3/1957 | United Kingdom . |

OTHER PUBLICATIONS

John G. Knapp et al., Fixed Mandibular Complete Denture Prosthesis Support by Mandibular Staple Bone Plate Implant, pp. 73–76.

Irwin A. Small et al., Mandibular Staple Bone Plate a Reconstructive Operation for the Atrophic Edentulous Mandible, pp. 10–14.

*Primary Examiner*—Michael Buiz
*Assistant Examiner*—Julian W. Woo
*Attorney, Agent, or Firm*—Young & Basile, P.C.

[57] ABSTRACT

A drill guide for mandibular staples is disclosed which is adapted to accurately align a drill for drilling fastener holes in the mandibular lower jaw portion at precisely located positions for the attachment of fasteners therethrough by a staple to retain a dental appliance in secure position on the mandibular jaw portion. The drill guide improves upon previously known devices for ensuring accuracy of drilling holes, while including members for attachment and locking, adjustability of the invention, cooling and cleaning, and assuring adequate bone material for drilling.

27 Claims, 2 Drawing Sheets

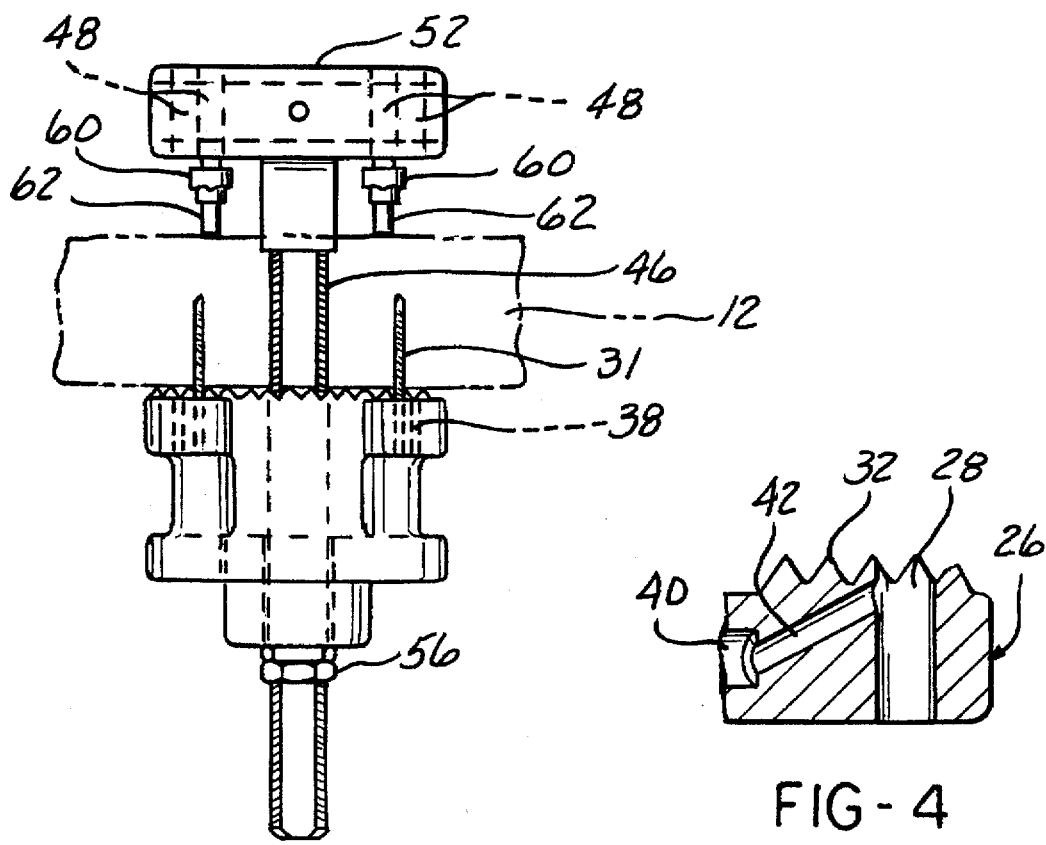
FIG-2
FIG-4
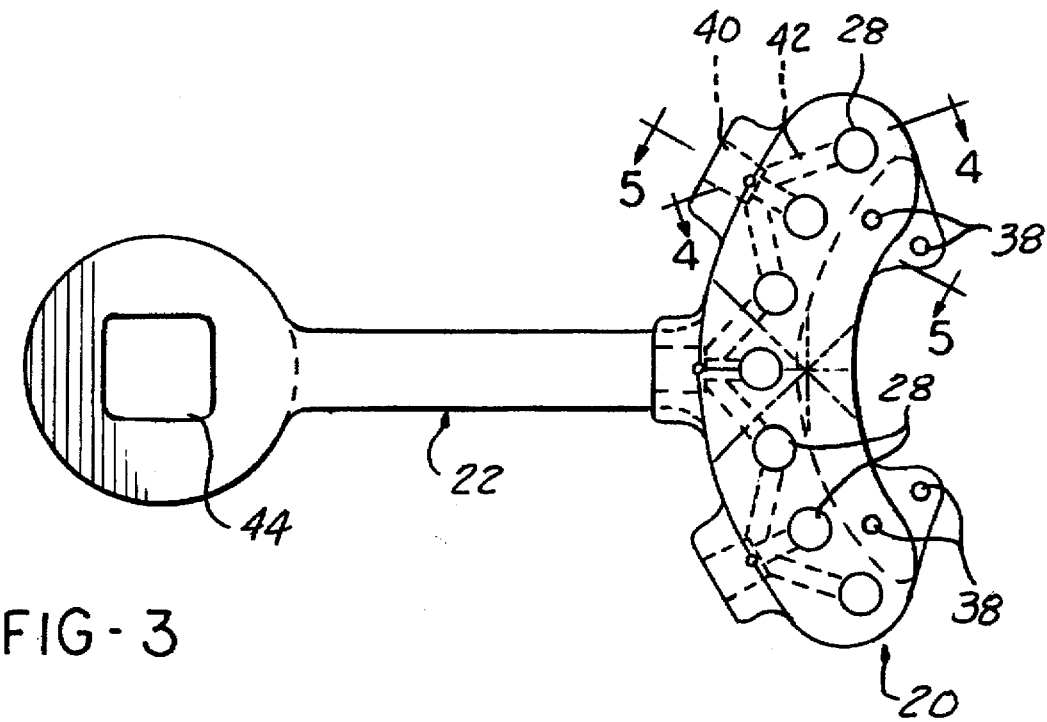
FIG-3

DRILL GUIDE FOR MANDIBULAR STAPLE TRANSOSSEOUS IMPLANTS

FIELD OF THE INVENTION

The present invention relates to a drill guide for mandibular staple transosseous implants and specifically for controlling the accuracy of drilling positions and assuring adequate bone material for drilling. The drill guide provides an accurate means for guiding the drilling of apertures through a mandibular jaw bone, be it human or animal, in which apertures at accurately spaced points are adapted to receive a mandibular staple transosseous implant provided with fastening means thereon to securely engage the jaw bone and to provide an interlock with the dental appliance normally, removably mounted on the jaw bone.

BACKGROUND OF THE INVENTION

Heretofore, in the use of dental appliances of a removable nature, particularly with reference to the lower mandibular jaw, natural suction of the dental appliance or cohesion is often reduced due to the aging and wasting away of jaw bone tissue. Various means are known to be employed in an effort to retain and anchor the lower removable dental appliance against accidental dislodgement from the jaw bone. Since the use of adhesives or known mechanical devices heretofore have been ineffective and inefficient for the intended purpose, a mandibular staple, such as disclosed in U.S. Pat. No. 4,906,189, has been developed for securing dental appliances to the jaw. However, the known means used in securing the mandibular staple lacks the accuracy desired in drilling the holes in the jaw bone for placement of the mandibular staple.

In the prior art patents (U.S. Pat. No. 3,414,975 and U.S. Pat. No. 3,664,022), a drill fixture or guide is provided in which a drill is guided through apertures through the jaw bone to allow placement of a mandibular staple. U.S. Pat. No. 3,664,022 improved upon the accuracy of the drill guide U.S. Pat. No. 3,414,975 by providing an apertured curvulinear abutment and spaced guide pins which are free to accommodate for unevenness in the jaw bone. However, these drill guides do not provide means for controlling the accuracy of the direction of the drill or ensuring that there will be adequate bone material for the drilling procedure and placing the staple.

The prior art disclosed in U.S. Pat. No. 3,664,022, also improved prior drill guides by allowing space on one side of the drill by providing a central slot that allows bone matter to escape. However, one wall of the drilling apertures is closed, and although somewhat relieved, clogging is still a concern.

The prior art does not disclose any means for cooling and cleaning of the drill guide apertures.

SUMMARY OF THE INVENTION

The present invention consists of an improved drilling guide which has a set of guide pins that extend upwardly from the drill guide portion and rest against the inner edge of the jaw bone. The guide pins act as a visual indicator of the distance between the guide pin and the center line of the drill guide aperture to control the accuracy of the drill ending point. The set distances from the center line of the drill to the guide pins, and from the drill centerline to the support rod allow the user to simply attach the drill guide to the jaw bone, and since the guide pins rest against the inside surface of the jaw bone, the user is assured adequate lateral bone material when drilling.

The improved invention also provides a simple means for attaching and locking the drill assembly to the jaw bone, consisting of a square shaped threaded support rod that is adapted to fit into a correspondingly square shaped opening of a lower arm on which the drill guide is located. The square shape of the support rod prevents the support rod from rotating, thus maintaining the lower arm member and the drill guide portion properly aligned and securely positioned. A lock nut is threadingly engaged onto the support rod allowing the user to move the lower arm member upward and downward along the support rod to the desired position and to lock the lower arm member in place while preventing relative rotation of the lower arm member and support rod.

The present invention improves upon the cleaning and cooling of the drill guide portion during the drilling operation. The drill guide portion contains ports connected to the drilling guide bores, or apertures, allowing coolant (i.e. water) to flow into the drill bores, cooling and cleaning the drilled area.

Another improvement concerns the recessed portion of the drill guide portion member that laterally intersects the apertures. In the present improved invention, a lateral slot surrounds the apertures permitting bone substances removed through the drilling operation through the jaw bone to be expelled outwardly on all sides of the drill to prevent clogging of said apertures.

It is therefore an object of the present invention to provide a means that allows improved accuracy of drilling holes needed to secure the mandibular staple to the mandibular jaw bone beneath the subcutaneous tissue.

Other objects, advantages and applications of the present invention will become apparent to those skilled in the art of drilling guides when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 2 is a rear view of the present improved invention in attached drilling position with the jaw bone in phantom as seen from line 2—2 in FIG. 1;

FIG. 3 is a top plane view of the lower arm and drill guide of the present improved invention, with the gripping teeth removed for clarity;

FIG. 4 is a cross sectional view of the drill guide taken along line 4—4 of FIG. 3;

DESCRIPTION OF THE PREFERRED EMBODIMENT

Figure 1:
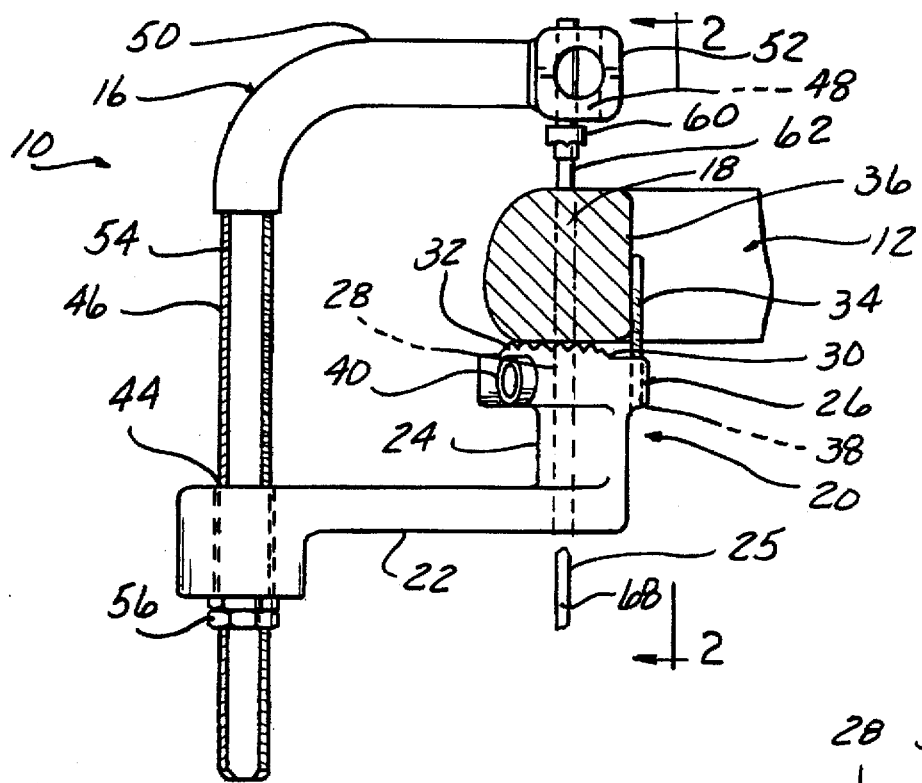
FIG. 1 is a side elevational view of the present improved mandibular drill guide illustrated in attached drilling position on the curvulinear front end of the mandibular jaw bone.
Figure 6:
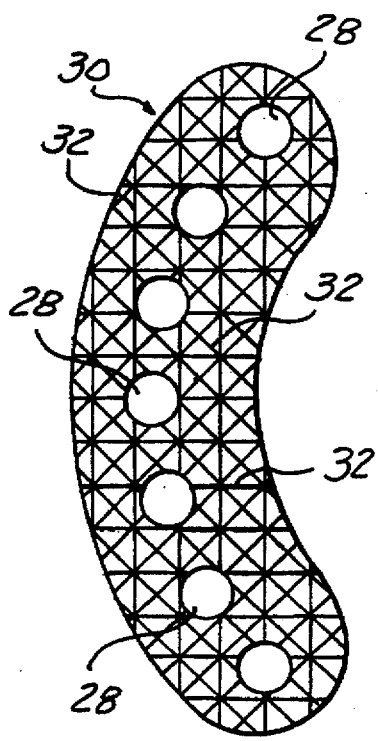
FIG. 6 is a top plane view of the gripping teeth on the drill guide.

Referring now to the drawings, and in particular to FIG. 1, where the present invention is illustrated, as a drill guide assembly 10 attached to a mandibular jaw bone 12 which could be either human or animal. The drill guide assembly 10 comprises a drill guide member 20 and a drill guide clamp 16. The drill guide assembly 10 allows accurate drilling of bores or holes 18 in the jaw bone 12 to effect the placement of a mandibular staple (not shown) such as shown in U.S. Pat. No. 4,906,189 which is incorporated by reference.

For this purpose, the drill guide member 20 has an elongated arm member 22 which supports the drill guide member 20. The drill guide member 20 contains a recess 24 and a top portion 26. Drill guide member 20 is curvulinear in shape and is provided with a plurality of apertures 28. The apertures 28 in the drill guide member 20 are adapted to guidingly receive drills of different sizes for drilling bores 18 in the mandibular jaw bone 12 for attachment of the staple and thus corresponding in the spacing and number to the spacing and number of locking pins and fastener rods of the mandibular staple (not shown).

Figure 5:
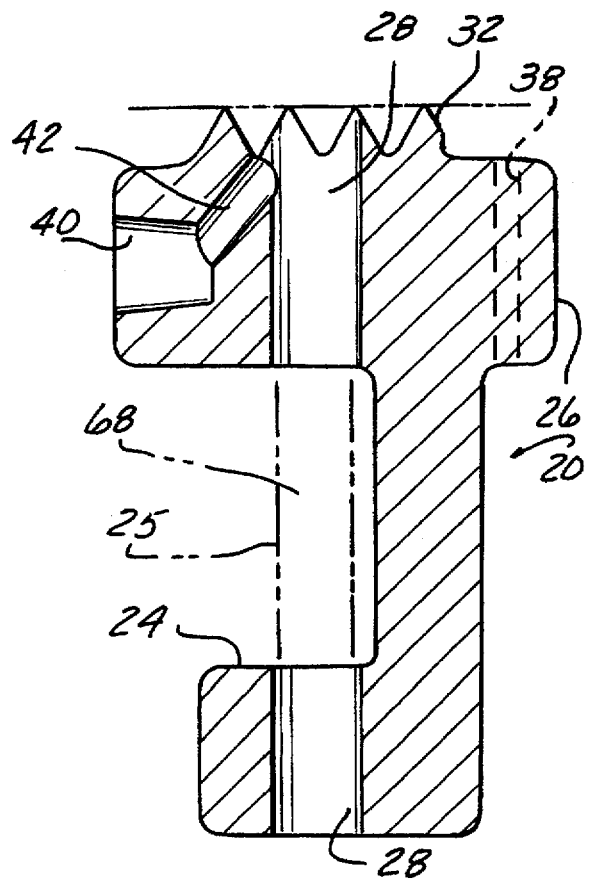
FIG. 5 is a cross sectional side view of the drill guide taken along line 5—5 in FIG. 3.

This curvulinear shape of the drill guide member 20 corresponds to the curvulinear shape of the support plate of the staple. As seen in FIG. 5, the drill guide member recess 24 completely intersects the apertures 28 to provide a lateral opening on all sides of the apertures 28. When drilling through the apertures 28, the drill 25 (shown in phantom line in FIG. 5) is free on all sides with respect to the aperture 20, thereby permitting powdered bone material and bone chips to be expelled during the drilling operation and not accumulate and/or clog the apertures 28.

The upper surface 30 of the top portion 26 of the drill guide member 20 is provided with rows of upwardly protruding gripping teeth 32 extending along the opposed outer edges of the top portion 26. The drill guide assembly 10 is adapted so that the gripping teeth 32 of the top portion 26 bite into the lower surface of the jaw bone 12, upon respective adjustment of the drill guide member 20, described further herein.

As shown in FIGS. 1 and 2, the top portion 26 of the drill guide member 20 is also provided with a set of guide pins 34, which extend upwardly from the top portion 26 into the space adjacent the rear facing surface of the jaw bone 12, resting on the surface of the jaw bone material 36. The guide pins 34 are placed in pin holes 38 in the top portion 26 of the drill guide member 20. Several sets of pin holes 38 are present to allow adjustable locations of entry for the guide pins 34 to adapt to different sizes of jaw bones. The guide pins 34 are also threaded to allow adjustment upwards and downwards through the pin holes 38. The purpose of the guide pins 34 is explained hereinafter.

As shown in FIGS. 4 and 5, the top portion 26 of the drill guide member 20 further contains port holes 40. Each of the port holes 40 are connected to the apertures 28 by passageways 42, which are interconnected, as shown in FIGS. 3. The port holes 40 allow passage of a cooling or cleaning fluid, such as water, through the passageways 42 to the apertures 28. Therefore, the ports 40 provide a means to cool the apertures 28 shortly after or during the drilling of the drill holes 18 in the jaw bone 12. Further, the port holes 40 provides a means to clean the apertures 28 by allowing a cleaning solution to rinse the apertures 28 after or during the drilling of the hole 18 through the jaw bone 12, and thus flushing out material through the port hole 40 as well as through the recess 24 of the drill guide member 20.

Referring now to FIGS. 1 and 3, the elongated arm member 22 of the drill guide member 20 has a square shaped opening 44 which corresponds in size and shape to receive the support rod member 46 of the drill guide clamp 16, thereby connecting the drill guide member 20 and the drill guide clamp 16.

The drill guide clamp 16 consists of a support rod member 46 and an upper arm member 50 containing a yoke member 52 thereupon. The support rod member 46 is threaded at 54 and square in shape so as to fittingly correspond with the opening 44 of the elongated arm member 22 of the drill guide member 20. A pair of nuts 56 are threadingly engaged to the support rod member 46 beneath the opening 44. The nuts 56 can be turned around the threaded portion 54 of the support rod member 46 to permit movement of the drill guide member 20 upwards or downwards along the support rod member 46, the nuts 56 also acting as a lock when the drill guide member 20 is set in the desired position. Also, since the support rod member 46 is designed in a square shape that fits through the corresponding square opening 44 of the elongated arm member 22, it cannot rotate once the drill guide member 20 is set in its desired position by the nuts 56.

The front end of the upper arm member 50 supports a yoke member 52 which extends transversely of the arm 50 to both sides thereof. Both outer ends 58 and 59 of the yoke member are formed cylindrically and each supports a locator pin 60 for extension downward toward the drill guide member 20. The locator pins 60 are yieldably supported for relative longitudinal up or down movement by a common pivot for reciprocating movement in opposite directions, and are located at opposite ends of the yoke member 52. This movement of the locator pins 60 is provided to accommodate for unevenness in the jaw bone thickness. The yoke member 52 allows lateral adjustment of the locator pins by providing a choice of placement holes 48 in which to place the locator pins to adjust to different jaw sizes. The lower ends of each of the locator pins 60 carry a toothed abutment 62, for a purpose which will appear hereafter. The pivotal locator pins 60 are positioned in vertical alignment with the respective outer end apertures 28 of the drill guide member 20, for a purpose to appear.

In use of the present improved mandibular drill guide assembly 10 for application of the staple (not shown), the initial step includes making a plaster mold of the arcuate front portion of the lower mandibular jaw of the patient and a clear plastic template corresponding to the gum portion of the denture (not shown). The template is then bored at two spaced locations at a predetermined distance such as to be clear of and between the exposed nerve centers on both sides of the jaw bone 12. The spacing between the apertures and the template (not shown) are intended to correspond to the actual spacing of the opposed securing rod of the selected staple (not shown). From this predrilled mold and template, the proper drill guide assembly 10 can be selected and checked for accuracy by attaching the drill guide assembly 10 to the mold and template and locating the two opposite locator pins 60 in the space bore provided in the template on the jaw mold. The locator pins 60 are laterally adjustable by placing the pins 60 in the appropriate placement holes 48. Since the locator pins 60, as previously described, are in vertical alignment with the outer end apertures 64 of the apertures 28 of the drill guide portion 20, accurate selection of the proper drill guide assembly 10 can be made for accurate drilling of the bores 18 through the front jaw bone 12 portion between the open nerve centers. Further, the guide pins 34 on the drill guide portion 20 are placed in the appropriate pin holes 38 according to the size of the jaw bone 12, and are threadingly adjusted into the jaw bone 12. The guide pins 34 rest on the side of the jaw bone material 36 and are parallel to the support rod member 46 and the alignment of the locator pins 60 and the outer end apertures of the plurality of apertures 28 of the drill guide member 20, where the drill holes 18 are drilled. The guide pins 34 ensure adequate bone material is present for drilling. The distance between the centerline of the drill 68 and the guide pins 34 is equal throughout the drilling of the jaw bone 12, thereby assuring adequate bone material when the pin is appropriately positioned.

With more particular reference to FIG. 1, the drill guide assembly 10 is then attached to the curved front end of the lower jaw bone 12 of the patient after first pulling back the tissue around the portions of the jaw bone which are to be drilled. The elongated arm member 22 of the drill guide member 20 is adjusted so that the top portion 26 of the drill guide portion 20 abuts against the underside of the curved front portion of the jaw bone 12 to clamp the jaw bone portion between the drill guide member 20 and the locator pins 60 which accurately mark the position for the extension of the securing rods of the staple through the jaw bone 12. The surface teeth 32 of the drill guide member 20, in attached position, bite into the jaw bone 12 to prevent lateral or rotational displacement of the drill guide assembly 10 during the drilling operation. The guide pins 34 are also placed into the jaw bone 12 and the distance between the centerline of the drill 68 and the guide pin 34 stands as a visual measure to ensure that there is adequate bone material for drilling. As previously mentioned, the curvature of the drill guide portion 20 corresponds substantially with the curvature of the front end of the mandibular jaw bone to properly drill the apertures 18 for the staple along the arcuate path. After the drill guide assembly 10 has been attached to the lower mandibular jaw bone 12 of the patient as described above, a drill 25 of the proper size is then used to drill the apertures 18 in the jaw bone 12 which are adapted to receive the rods and pins of the staple. The drilling of the apertures 18 and the insertion of the staple remains the same as described in my U.S. Pat. No. 4,906,189.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A drill guide assembly for drilling a plurality of apertures in accurately located positions through a jaw bone to receive a mandibular staple, said drill guide assembly comprising:

a first, arcuate, generally planar member having a plurality of spaced drill-guiding apertures extending therethrough, and positionable on a lower surface of said jaw bone;

at least one locator pin positionable on the upper surface of said jaw bone;

means connecting the first member and the locator pin for clampingly engaging the jaw bone between the first member and the locator pin; and a guide pin projecting outwardly from the first planar member and generally toward said locator pin, and said guide pin positionable against an inside surface of the jaw bone providing a predetermined distance between the drill-guiding apertures and said inside surface of said law bone thereby ensuring adequate bone material for drilling through one of said apertures.

2. The drill guide assembly as defined in claim 1, wherein said means connecting said first member and said locator pin further comprises:

an L-shaped clamp including an upper arm supporting a yoke member carrying a plurality of locator pins, and a threaded support rod.

3. The drill guide assembly as defined in claim 2 further comprising:

an arm member supporting the first member at one end and providing an opening at the opposite end, said opening of said arm member corresponding in shape to the support rod, allowing the arm member to engage the support rod for longitudinal movement along said support rod to define clamping means for clampingly engaging said jaw bone between the first member and the at least one locator pin, said clamping means allowing the drill guide assembly to adjust to different jaw sizes.

4. The drill guide assembly as defined in claim 3, further comprising:

a pair of nuts engageable with said threaded support rod, said nuts moveable longitudinally along the rod beneath the arm member supporting the first member to define locking means for holding the arm member in any desired position along the longitudinal length of the support rod.

5. The drill guide assembly as defined in claim 4, further comprising:

said support rod having an elongated length with a square cross-sectional shape to slidingly engage with respect to said corresponding opening in said arm member supporting the first member for longitudinally adjusting said arm member to any desired location along said longitudinal length of said support rod the square cross-sectional shape of said support rod and said opening preventing rotation of said first member with respect to said support rod.

6. The drill guide assembly as defined in claim 5, further comprising:

said first member having at least one port connected to said apertures by at least one passageway, said at least one port providing means for cooling and cleaning of the apertures by allowing fluid flow through said drill-guiding apertures.

7. The drill guide assembly as defined in claim 6, further comprising:

said first member having a recessed portion providing only top and bottom support for said apertures on said first member, said recess portion defining means for permitting bone substances removed during the drilling operation through said jaw bone to expel outwardly on all sides of the drill, for avoiding clogging of said apertures by removed material between the drill and the supporting walls of the first member.

8. The drill guide assembly as defined in claim 7, further comprising:

said first member having a plurality of guide pin apertures to allow adjustment of said guide pin to fit the jaw to be drilled.

9. The drill guide assembly as defined in claim 8, further comprising:

a plurality of guide pins, each of said guide pins threaded to allow adjustment upwards and downwards through said plurality of pin apertures of said first member.

10. The drill guide assembly as defined in claim 9, further comprising:

said yoke member providing a plurality of apertures for lateral adjustment of said at least one locator pin.

11. The drill guide assembly as defined in claim 1, further comprising:

said first member having at least one port connected to said drill-guiding apertures by at least one passageway and said at least one port providing means for allowing flow of liquid into the drill-guiding apertures to provide cooling and cleaning of the drill-guiding apertures.

12. The drill guide assembly as defined in claim 1, further comprising:

said first member having a recessed portion providing only top and bottom support for said drill-guiding apertures on said first member, said recessed portion defining means for permitting bone substances removed during the drilling operation through said jaw bone to expel outwardly on all sides of the drill, for avoiding clogging of said drill-guiding apertures by removed material between the drill and the supporting walls of the first member.

13. The drill guide assembly as defined in claim 1, further comprising:

said first member having a plurality of guide pin apertures to allow adjustment of said guide pin to fit the jaw to be drilled.

14. The drill guide assembly as defined in claim 13, further comprising:

a plurality of said guide pins, each of said guide pins being threaded to allow adjustment upwards and downwards through said plurality of guide pin apertures formed in said first member.

15. The drill guide assembly as defined in claim 3, further comprising:

said first member having at least one port connected to said drill-guiding apertures and said at least one port providing means for allowing flow of fluid into the drill-guiding apertures to provide cooling and cleaning of the drill-guiding apertures.

16. The drill guide assembly as defined in claim 3, further comprising:

said first member having a recessed portion providing only top and bottom support for said drill-guiding apertures on said first member, said recess portion defining means for permitting bone substances removed during the drilling operation through said jaw bone to expel outwardly on all sides of the drill, for avoiding clogging of said drill-guiding apertures by removed material between the drill and the supporting walls of the first member.

17. The drill guide assembly as defined in claim 3, further comprising:

said first member having a plurality of guide pin apertures to allow adjustment of said guide pin to fit the jaw to be drilled.

18. The drill guide assembly as defined in claim 17, further comprising:

a plurality of guide pins, each of said guide pins threaded to allow adjustment upwards and downwards through said plurality of pin apertures of said first member.

19. The drill guide assembly as defined in claim 3, further comprising:

said yoke member providing a plurality of apertures for lateral adjustment of said at least one locator pin.

20. In an apparatus for guiding a drill during a drilling procedure to produce at least one aperture in an accurately located position through a jaw bone of a patient for implantation of a mandibular staple therethrough, said apparatus including a first member having a plurality of drill-guiding apertures extending therethrough, and a second member opposing said first member, said first member moveable with respect to said second member along a fixed path into a clamping position with said first and second members clampingly engaging opposite faces of said jaw bone with said jaw bone interposed between said first and second members, the improvement comprising:

lateral locator means supported by said first member and extending outwardly toward said second member, said lateral locator means engageable with an external surface of said jaw bone extending transversely between said opposite faces for laterally locating said first and second members with respect to said jaw bone so that said drill-guiding apertures are spaced a predetermined distance from an edge of said jaw bone for ensuring sufficient jaw bone material in a lateral direction to drill apertures for receiving said mandibular staple and for anchoring said mandibular staple in said apertures after said drilling procedure.

21. The apparatus of claim 20 further comprising:

said first member having a plurality of locator-receiving apertures; and said lateral locator means including at least one lateral locator pin selectively and releasibly engageable with any one of said locator-receiving apertures, said locator-receiving aperture selected to provide a predetermined lateral spacing of said drill-guiding apertures with respect to said external surface of said jaw bone extending transversely between said opposite faces of said jaw bone.

22. The apparatus of claim 20 further comprising:

fluid passage means extending through said first member and in fluid communication with each of said drill-guiding apertures for cooling said drill during said drilling procedure and for flushing material from said drill-guiding apertures during said drilling procedure.

23. The apparatus of claim 22 further comprising:

said fluid passage means including a slot extending transversely with respect to said drill-guiding apertures, said slot dividing each drill-guiding aperture into first and second coaxial portions spaced longitudinally from one another.

24. The apparatus of claim 20 further comprising:

complementary shaped means for preventing rotation of said first and second members with respect to one another.

25. The apparatus of claim 24 further comprising:

said complementary shaped means for connecting said first and second members to one another and for guiding movement of said first and second members with respect to one another along a fixed path into said clamping position.

26. The apparatus of claim 24 wherein said complementary shaped means includes an elongated member having a non-circular cross section connected to one of said first and second members and an aperture having a non-circular cross section complementary with respect to said elongated member, said aperture formed in the other of said first and second members.

27. The apparatus of claim 20 further comprising:

means for locking said first and second members in said clamping position with respect to said jaw bone.

* * * * *